(12) United States Patent
Forsyth, III (10) Patent No.: US 6,394,103 B1
(45) Date of Patent: May 28, 2002

(54) DENTAL FLOSSING TOOL

(76) Inventor: Roland Forsyth, III, 631 Brier St., Kenilworth, IL (US) 60043

( * ) Notice: Subject to any disclaimer, the term of this patent is extended or adjusted under 35 U.S.C. 154(b) by 0 days.

(21) Appl. No.: 09/666,756

(22) Filed: Sep. 21, 2000

(51) Int. Cl.⁷ ................................................ A61C 15/00
(52) U.S. Cl. ..................................... 132/323; 132/326
(58) Field of Search ................................. 132/323–326

(56) References Cited

U.S. PATENT DOCUMENTS

| | | | |
|---|---|---|---|
| 1,582,000 A | * | 4/1926 | Gesell |
| 1,916,653 A | | 7/1933 | Bodde |
| 2,117,844 A | | 5/1938 | Grieco |
| 2,176,069 A | | 10/1939 | Goulet |
| 2,873,749 A | * | 2/1959 | Gjerde |
| 3,799,177 A | | 3/1974 | Bragg |
| 3,882,879 A | * | 5/1975 | Lucas |
| 3,906,963 A | | 9/1975 | Jenkins et al. |
| 3,910,294 A | * | 10/1975 | Reed |
| 4,495,957 A | * | 1/1985 | Beggs et al. |
| 5,105,840 A | * | 4/1992 | Giacopuzzi ................ 132/325 |
| 5,183,065 A | * | 2/1993 | Mason ....................... 132/323 |
| 5,287,865 A | * | 2/1994 | Fulton ....................... 132/323 |
| 5,423,338 A | * | 6/1995 | Hodge et al. ............... 132/324 |
| 5,819,769 A | * | 10/1998 | Gutierrez .................... 132/327 |
| 6,079,424 A | * | 6/2000 | Lillbacka .................... 132/326 |
| 6,092,536 A | * | 7/2000 | Owens ........................ 132/325 |

OTHER PUBLICATIONS

American Dental Association, Flossing Basics, 1998.
The John O. Butler Company, Butler Gum Full Line Catalog, p. 18, 1999.

* cited by examiner

*Primary Examiner*—Ralph A. Lewis
(74) *Attorney, Agent, or Firm*—Philip M. Kolehmainen

(57) ABSTRACT

A mechanism with a handle supports a pair of forwardly extending arms with a pair of guides flanking a flossing gap at the front of the tool. Clamp members anchor ends of a length of floss at the handle. An adjuster is moved to alter the length of the floss path in the tool so that the floss at the flossing gap can be configured as a straight line or in a loop with variable tension. A leverage bite member is mounted between the arms for sliding and rotating motion.

27 Claims, 5 Drawing Sheets

DENTAL FLOSSING TOOL

FIELD OF THE INVENTION

The present invention relates to an improved dental flossing tool.

DESCRIPTION OF THE PRIOR ART

Flossing to remove bacteria containing plaque between teeth and below the gum line is an important aspect of dental hygiene because plaque removal can reduce the incidence of health problems including tooth decay and gum disease. It can be difficult and unpleasant to floss manually because of the need to use two hands in awkward motions and the necessity to place fingers in the mouth. As a result there has long been a need for a practical, effective flossing tool. This need has never been successfully met.

The most common type of known dental flossing holder is a one-piece molded plastic fork having a handle and spaced arms with tips separated by a gap. The user secures the ends of a length of floss, for example by wrapping them around a knob near the handle, with the floss held in a straight line and taut across the gap. This holder is intended to make flossing easier than when done manually and to eliminate the need for the user to use two hands and to place fingers in the mouth. However this holder has disadvantages.

Effective flossing requires that the floss be in a straight line or taut in some instances such as when inserted between closely spaced teeth, but be in a loop under variable tension in other instances such as when it is desired to wrap the floss partially around a tooth and wipe or sweep the tooth surface. With known fork holders, the floss path length cannot be adjusted to provide both straight line and looped floss in the gap and the tension of the floss in the gap cannot be varied. It would be desirable for a flossing tool to provide an easy way for the user to adjust the configuration and the tension of the floss in the flossing gap.

When flossing, the user must force the floss into the inter dental crevices between adjacent teeth. This can require substantial force, especially when the adjacent teeth are closely spaced. With manual flossing there is no mechanical advantage to assist this motion. With the known fork holder, there is a limited mechanical assist resulting from the cantilever length of the holder, but the effect is limited. It would be desirable for a flossing tool to provide an effective mechanical advantage making it easy for the user to generate and control the necessary entry force at various positions in the mouth.

During flossing, a fresh segment of floss should be used at each site. Another problem with the known fork holder is that it is difficult to provide clean floss in the flossing gap because this requires repeatedly unsecuring and resecuring the floss after each site is cleaned. When the floss is anchored around a knob, it must be unwrapped and then rewrapped after each inter tooth crevice is cleaned. As a result the tendency is for a soiled segment of floss to be reused.

It has been proposed to provide a powered flossing tool in order to automatically advance fresh floss into position. For example it has been suggested that a motor might take up soiled floss while reeling out fresh floss. Such a tool would be subject to the disadvantages of complexity and high cost.

SUMMARY OF THE INVENTION

A principal object of the present invention is to provide an improved dental flossing tool. Other objects are to provide a dental flossing tool with which the floss path length can be adjusted to provide either a straight line or a loop configuration of floss with variable tension in a flossing gap; to provide a dental flossing tool with which it is convenient and easy to advance fresh floss into the flossing gap after each inter tooth site is cleaned; to provide a dental flossing tool offering effective mechanical advantage to assist the insertion of floss between teeth at various locations in the mouth; and to provide a dental flossing tool overcoming the disadvantages of known flossing aids.

In brief, in accordance with the invention there is provided a dental flossing tool including a handle and a tip spaced from the handle. The tip includes a pair of floss guides defining a flossing gap The tool provides a floss path including the flossing gap. A floss anchor structure holds a length of floss in the floss path. A floss path length adjuster varies the floss path length in order to alter the configuration and the tension of floss in the gap.

In brief, in accordance with another aspect of the invention, there is provided a dental flossing tool including a handle and a pair of arms extending from the handle. A pair of floss guides at the ends of the arms define a flossing gap. A floss anchor structure adjacent the handle holds the ends of a length of floss extending along a floss path including the floss guides and the flossing gap. A bite member is supported between the arms.

In brief, in accordance with yet another aspect of the invention, there is provided a dental flossing tool including a handle and a pair of arms extending from the handle. A pair of floss guides at the ends of the arms define a flossing gap. A floss anchor structure adjacent the handle holds the ends of a length of floss extending along a floss path including the floss guides and the flossing gap. The floss anchor structure includes a floss clamp having first and second relatively movable clamp jaws each having a floss engaging gripping surface.

BRIEF DESCRIPTION OF THE DRAWING

The present invention together with the above and other objects and advantages may best be understood from the following detailed description of the preferred embodiment of the invention illustrated in the drawings, wherein.

DETAILED DESCRIPTION OF THE PREFERRED EMBODIMENTS

Having reference now to the drawings, and initially to FIGS. 1–8, there is shown a dental flossing tool designated as a whole by the reference character 10 and constructed in accordance with the principles of the present invention. In general the tool 10 includes a handle portion 12 with which the user grips the tool 10 to perform a dental flossing procedure, and a pair of extending arms 14 that can enter the mouth of the user. At the forward end of each arm 14 is a floss guide 16 and between the guides 16 is a flossing gap 18 where a segment of dental floss 20 is supported for use in flossing a user's teeth.

An anchor structure generally designated as 22 grips spaced portions of the floss 20 to hold a length of floss 20 in a floss path 24. The anchor structure 22 permits the user to easily and quickly anchor the floss 20 in place, and alternatively to release the floss 20 so that a fresh segment of floss. 20 can be conveniently advanced into the flossing gap 18.

Figures 1, 5:
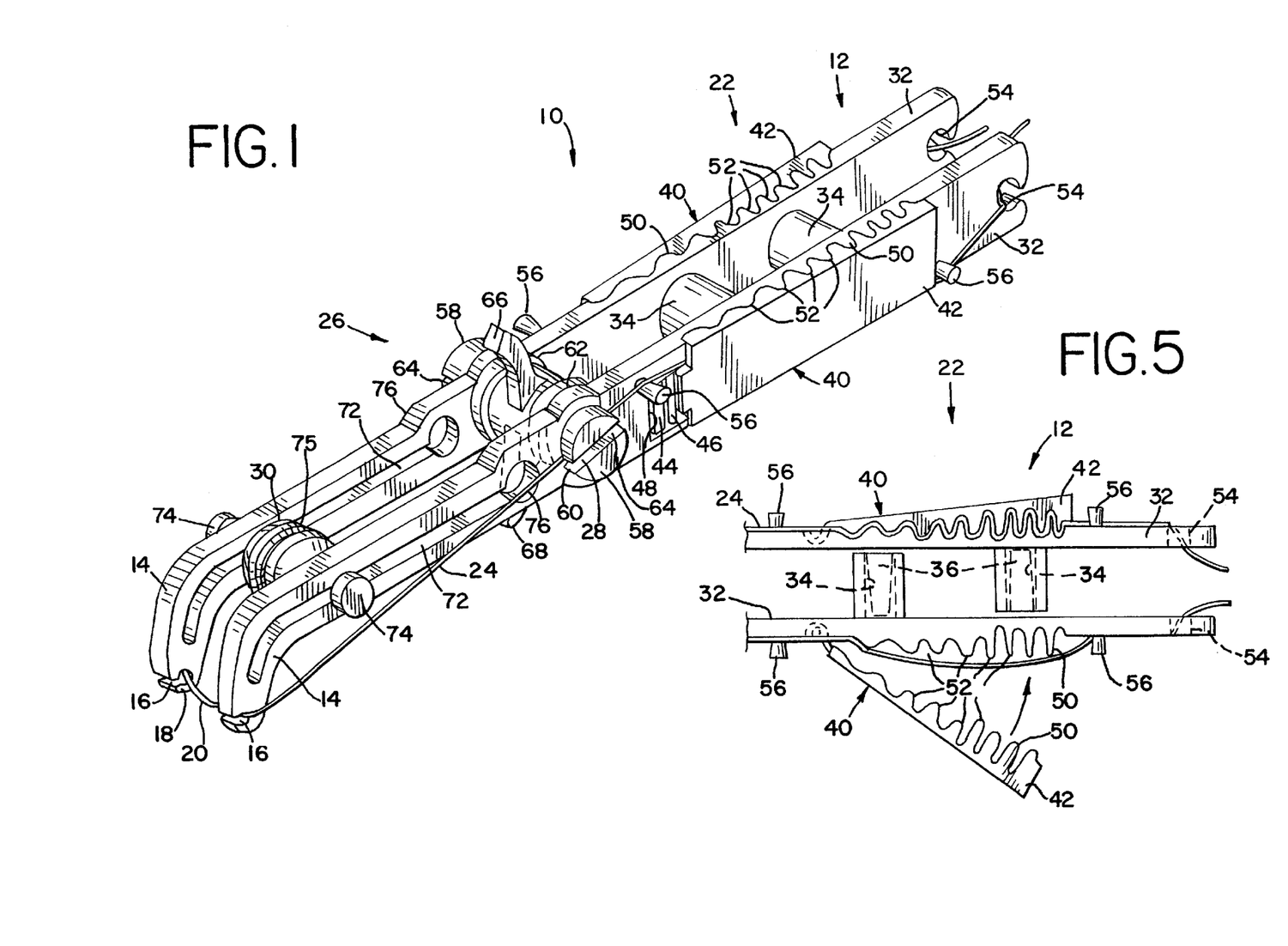
FIG. 1 is an isometric view of a dental flossing tool constructed in accordance with the present invention.
FIG. 5 is fragmentary top view illustrating the floss anchor structure of the dental flossing tool.
Figure 2:
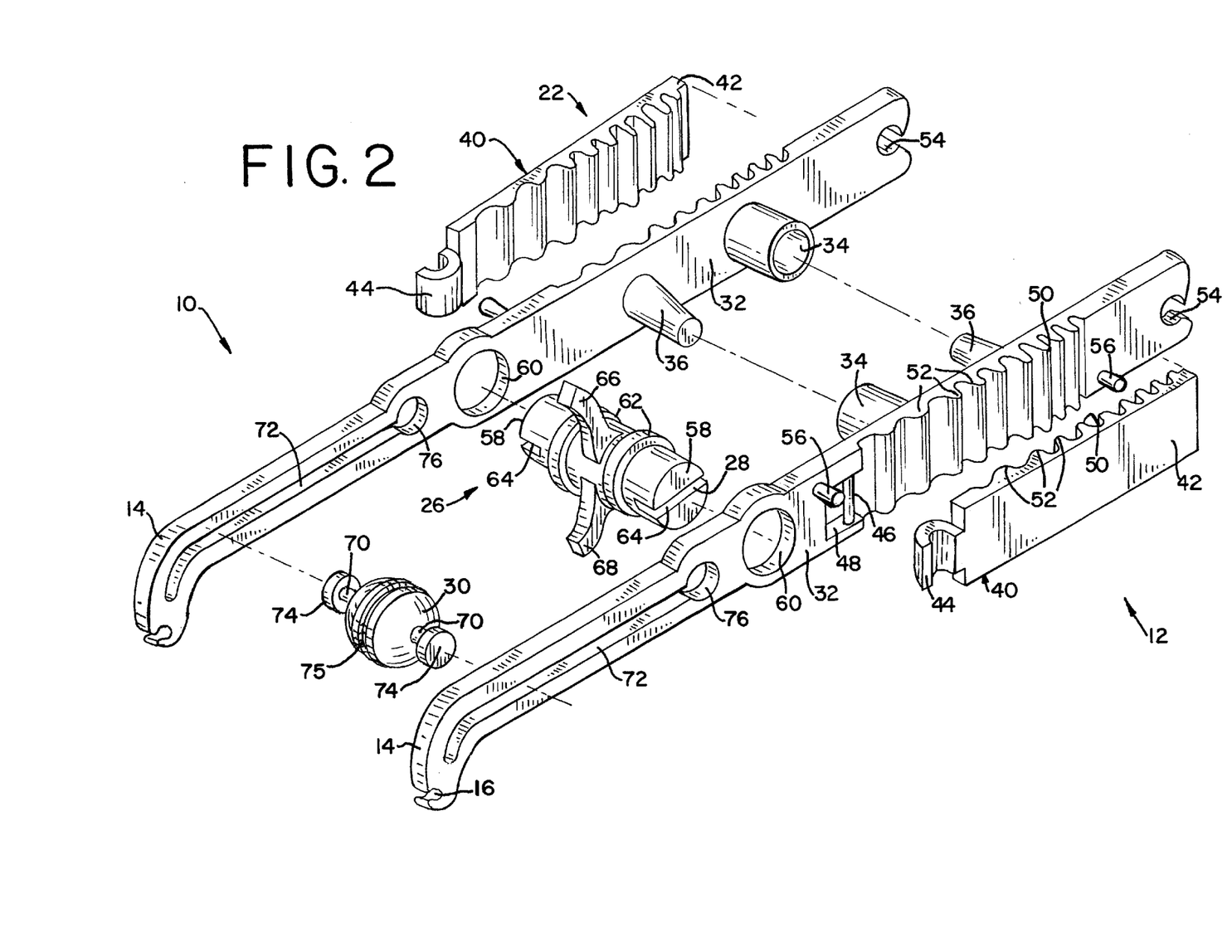
FIG. 2 is an exploded isometric view of the dental flossing tool.

A length adjuster generally designated as 26 includes a pair of floss passages 28 that are included as parts of the floss path 24. The length adjuster 26 can be moved by the user in order to move the floss passages 28 and thereby change the length of the floss path 24 in which the length of floss 20 is held. By increasing the length of the portion of the floss path outside the gap 18, the user decreases the amount and/or increases the tension of floss 20 present in the gap 18. Alternatively by decreasing the length of the portion of the floss path outside the gap 18, the user increases the amount and/or decreases the tension of floss 20 in the gap 18. This permits the user to control the tension of the segment of floss in the gap 18 and to configure the floss 20 in the gap 18 as a straight line (FIG. 7) or in a loop (FIG. 1).

A bite member 30 is carried between the arms 14 between the handle portion 12 and the flossing gap 18. The bite member 30 is mounted for both rotation and sliding movement between the arms 14. The user can hold the bite member 30 between the user's teeth and manipulate the handle portion in order to move the floss guides 16 and flossing gap 18 within the user's mouth. The slidable mounting of the tool 10 on the bite member 30 permits the user to advance or retract the flossing gap 18 to align the floss 20 with selected crevices between interfacing teeth prior to inserting floss and also to move the guides 16 around the base of either of the interfacing teeth while flossing. The pivotal mounting of the tool 10 on the bite member 30 provides a substantial mechanical advantage that makes it easy for the user to gently nudge the handle 12 to rock the floss 20 in a vertical direction between adjacent teeth in many locations in the mouth.

Proceeding now to a more detailed description of the structure and operation of the tool 10, in the embodiment of FIGS. 1–8 the tool 10 includes a body formed of two similar, parallel body rails 32. Each rail includes a socket 34 mating with a stud 36 on the other rail. The studs 36 and sockets 34 can have a snug, press fit or a snap fit, and when assembled together they hold the rails 32 in their parallel, spaced position. The rear portions of the rails 32 form the handle portion 12 of the tool 10, and the sockets 34 and studs 36 provide ample strength for gripping of the handle 12 by the user. The forward portions of the rails 32 form the arms 14.

The anchor structure 22 includes a pair of floss clamps 40, one associated with each of the rails 32. Each floss clamp 40 includes a clamp lever 42 having a curved mounting tab 44 pivoted behind a pin 46 in a recess 48 in the respective rail 32. The lever can pivot between open and closed positions seen respectively in the bottom and top portions of FIG. 5. Interfacing and mating clamp surfaces 50 are defined on the levers 42 and the outer surfaces of the rails 32 in the region of the handle 12. The surfaces 50 have rounded undulations 52 that are preferably generally sinusoidal.

Rather than being uniform throughout, the undulations 52 increase in amplitude or height and decrease in wavelength or spacing in the direction away from the pivot pin 46. A first group of undulations 52 nearest the pivot pin 46 have a relatively small height but are relatively widely spaced. A second group farther from the pivot pin 46 are taller and more closely spaced. A third group farthest from the pivot pin 46 are the highest and the most closely spaced. As the user grips the handle 12, the clamp surfaces 50 pivot together from the open position to the closed position, and the undulations 52 mesh to firmly capture the floss 20. This pattern of undulations also releases the floss 20 when the clamp surfaces 50 are spread apart only slightly.

The rear of each rail 32 includes a floss retaining recess 54 serving to loosely hold and position the floss 20 at the back of the tool 10. Guide pegs 56 are located at the rear and the front of the floss clamps 40. The pegs 56 are somewhat tapered to hold the floss 20 at the bases of the pegs. The pegs 56 position the floss along a somewhat inclined, non-axial line through the clamps 40. This increases the length of floss 20 engaged by the clamp surfaces 50 and thus increases the clamp force. In addition, this configuration permits the floss to exit from the clamps 40 to the sides of the recesses 48 so that there is no interference with pivotal motion of the levers 42. The rear pegs 56 resist the effect of gravity on the floss 20 when the tool 10 is inverted for flossing of teeth in the upper jaw.

The floss path 24 extends along the outer side surfaces of the rails 32 from the clamps 40 and over the forward guide pegs 56 to the floss guides 16 and flossing gap 18. When the clamps 40 are closed by the grip of the user, the amount of floss 20 in the floss path 24 is fixed because floss cannot slip or move axially in the floss clamps 40.

During flossing, it is highly desirable to be able to change the configuration and/or the tension of the floss 20 in the flossing gap 18. When floss is first inserted between adjacent teeth, the floss should lie in a straight line. However, after the floss is in place between the adjacent teeth, the floss should be in a loop shape to partly wrap tightly around either adjacent interfacing tooth as the floss is wiped vertically to remove plaque from the tooth. The length of floss 20 forming the loop, and thus the shape of the loop, should be variable to adapt to teeth of different sizes and shapes. Using the length adjuster 26, the user can easily change the floss configuration in the gap 18 to provide a straight line or loops of continuously variable length.

Figure 3:
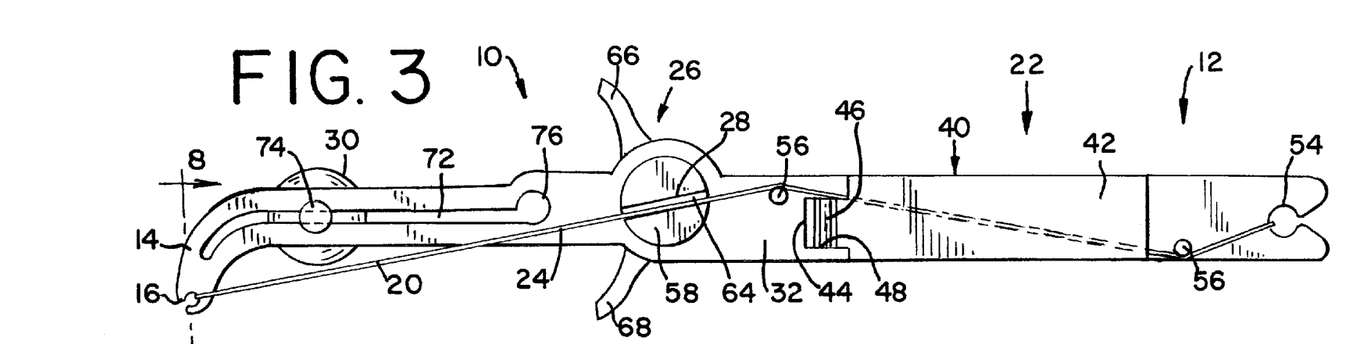
FIG. 3 is a side elevational view of the dental flossing tool.
Figures 4, 8:
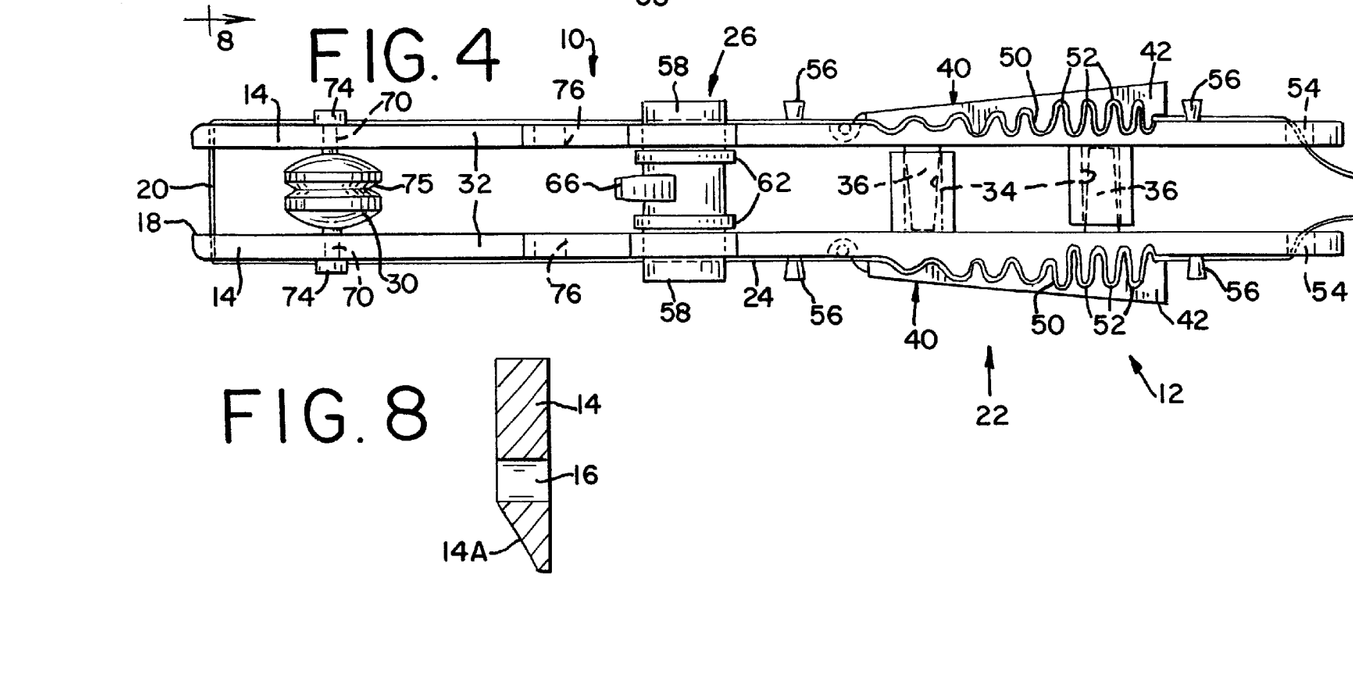
FIG. 4 is a top plan view of the dental flossing tool.
FIG. 8 is an enlarged fragmentary sectional view taken along the line 8—8 of FIG. 3.
Figures 6, 7:
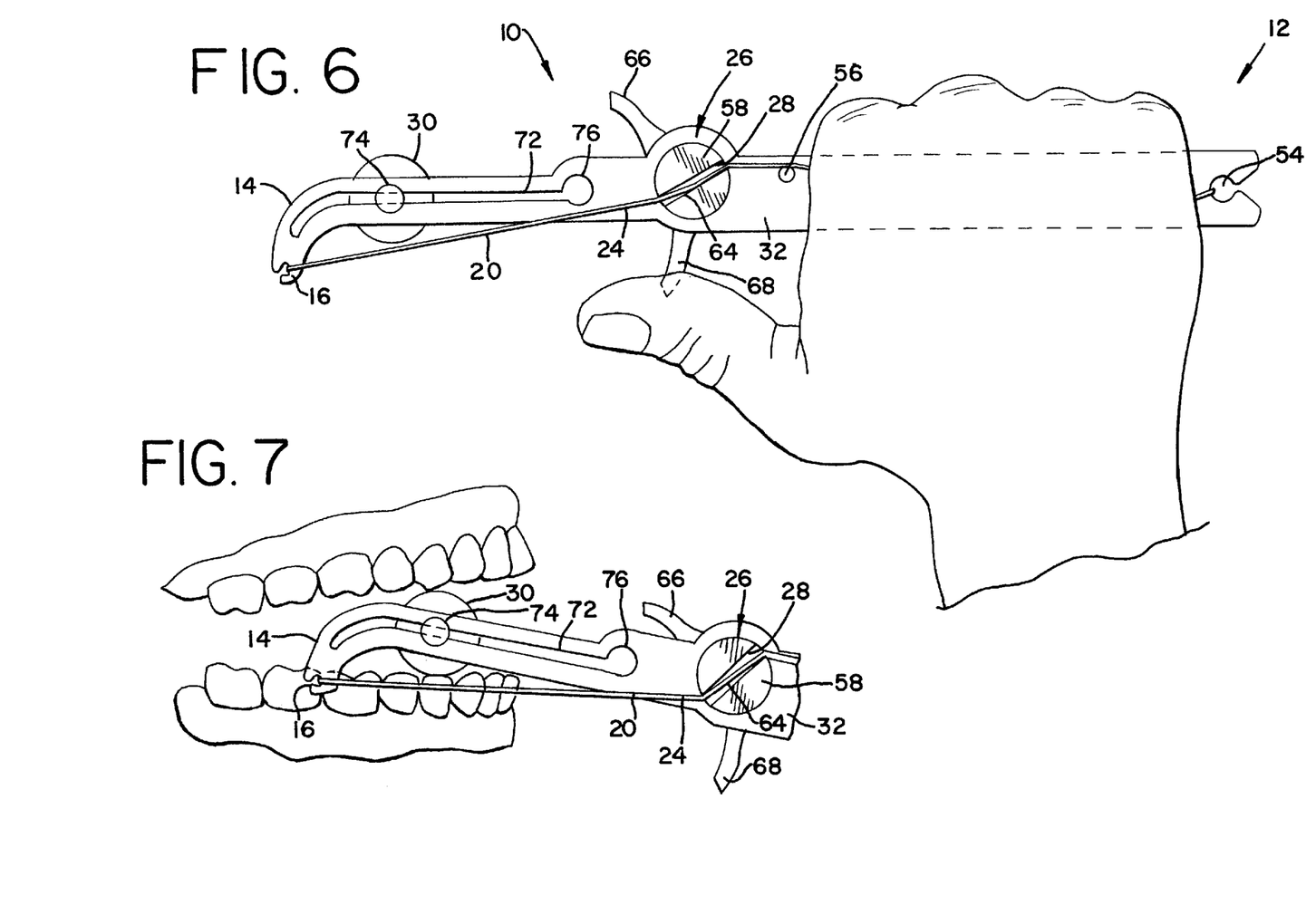
FIG. 6 is side view illustrating operation of the floss path length adjuster of the dental flossing tool.
FIG. 7 is a fragmentary side view illustrating the dental flossing tool in use.

The length adjuster 26 is a circular cylinder having spaced ends 58 journaled for rotation in openings 60 in the rails 32. A pair of flanges 62 are captured between the rails 32 to hold the adjuster 26 in position. Diametric slots 64 are formed in the opposed faces of the ends 58. The two slots 64 are parallel with one another in a plane including the axis of rotation of the adjuster 26 and each is aligned along a direct line extending from the top of the forward peg 56 to the guide 16. A pair of thumb cranks 66 and 68 extend generally radially from the center of the adjuster 26 between the flanges 62. The cranks 66 and 68 are rotationally offset from one another by about one hundred twenty degrees, and are symmetrical about a horizontal plane parallel to the major axial direction of the arms 14. When the flossing gap 18 is directed down for flossing teeth of the lower jaw, the crank 68 is located for convenient manipulation by the thumb of the user's hand when the user is grasping the handle 12 (FIG. 6). When the flossing gap 18 is directed up for flossing teeth of the upper jaw, the user's thumb engages the other crank 66. The slots 64 in the length adjuster 26 provide the passages 28 that form parts of the floss path 24. Rotation of the length adjuster 26 turns the slots 64, to move the floss passages 28 at an angle relative to the gap 18. This forms zig-zag path segments of variable length along the portions of the floss path 24 outside of the gap 18. The greater the rotation from the position seen in FIGS. 1 and 3, the longer the total length of floss path 24. When the adjuster is in the position seen in FIGS. 1 and 3, the floss path 24 has its shortest length. When rotated to an intermediate position as seen in FIG. 6, the floss path 24 is longer. When rotated fully to the position seen in FIG. 7, the floss path length is maximized. The user can manipulate the crank 66 or the crank 68 to rotate the adjuster 26 in a continuously varying manner between positions. To configure the floss 20 in a straight line at the gap 18, or to increase tension in the floss 20, the user increases the path length as seen in FIG. 7. To form a shallow or a deeper loop, or to decrease tension in the floss 20, the user decreases the floss length as seen in FIGS. 6 and 3. When the length adjuster 26 is repositioned, the portions of the floss path 24 at opposite sides of the gap 18 and along the arms 14 match in length to balance the change in length and/or tension of the floss 20 in the gap 18.

The floss 20 is subjected to tension when used in flossing. A force of a number of pounds can be needed to insert the floss 20 between closely spaced teeth, resulting in tension in the floss 20. Wiping of the floss 20 during flossing also requires force and also results in tension in the floss 20. The mechanical advantage provided by the geometry of the rotating slots 64 acting in concert with the torque amplification effect of the elongated thumb cranks 66 and 68 makes it easy for the user to use light thumb force to regulate and maintain the needed tension in the floss 20 whether the floss 20 in the gap 18 is in a straight line or in a loop. The tension across the gap 18 is evenly balanced between the guides 16.

When floss 20 is initially loaded into the tool 10, the length adjuster can be in the position seen in FIG. 3 with the slots 64 aligned with the guides 16 and the forward guide pegs 56. The user cuts a supply of floss 20 from the desired dispenser. The floss 20 should be at least a few inches longer than twice the length of the tool 10. The user can place the approximate center of the supply of floss 20 in the guides 16 and across the gap 18, and then the user can simply lay the floss along straight lines from the guides 16, into the slots 64 and over the forward pegs 56. There is no need to thread the floss 20 through restricted openings or along convoluted paths. With the clamp levers 42 in their open positions, the user can let go of the handle 12 and pinch the spaced ends 58 of the length adjuster 26 to hold the tool 10. Then the floss 20 can be laid between the clamp surfaces 50 and placed under the rear guide pegs 56 with the trailing ends loosely held in the retaining recesses 54. At least one of the free ends should be long enough to permit the floss to be advanced periodically by opening the clamps 40 to provide a fresh section of floss at the gap 18.

When the floss 20 is loaded, the floss 20 in the floss path 24 should be long enough to form of a loop in the gap 18 (FIG. 1) before the floss clamps 40 are closed. The user can accomplish this by forming the floss in the gap 18 into a loop shape and then closing the levers 42 with the adjuster 26 in the aligned position of FIG. 3. Alternatively, the user can rotate the adjuster 26 to the position of FIG. 7 before closing the clamps 40, and can then provide a loop by returning the adjuster to the position of FIG. 3.

The application and control of flossing forces to the teeth of the user is facilitated by the bite member 30. The bite member 30 is a wheel with opposed trunnions 70 received for sliding and for rotating movement in slots 72 in the arm portions 14 of the rails 32. Enlarged ends 74 of the trunnions 70 normally prevent the arms 14 from being separated. The user can grip the bite member 30 between the user's teeth as seen in FIG. 7 to support the tool in the user's mouth. The outer circumference of the bite member 30 is provided with a V-shaped groove 75 to assist in holding the bite member in place between teeth of the user. With the bite member 30 in a fixed position, the tool 10 is easily moved with one hand. The length of the slots 72 is sufficient to permit the flossing gap 18 to be aligned with any of several inter tooth gaps to the rear of the bite member 30 by sliding the rails 32 along the trunnions 70. The forward ends of the slots 72 are curved in the direction of the flossing gap 18 to permit the flossing gap 18 to be positioned close to the bite member 30.

When the floss 20 in the flossing gap 18 is aligned with a selected crevice between adjacent teeth, the flossing gap 18 can then be moved up and down by pivoting the rails 32 on the trunnions 70. The forward ends of the arm portions 14 of the rails 32 are curved or hooked to provide a vertical offset between the main portions of the rails 32 and the flossing gap 18. This offset as measured from the axial centerlines of the arms 14 to the top of the floss guides 16 is generally equal to the sum of the bite wheel radius plus half of the vertical distance required for flossing of a typical tooth. As a result, the handle 12 is centered in the horizontal position and interference between the rails 32 and the front teeth of the user is minimized.

As seen in FIG. 7, the axial distance from the center of the bite member 30 to the flossing gap 18 is smaller than the axial distance from the axis of the bite member 30 to the user's hand on the handle 12. The resulting mechanical advantage assists the user in easily applying a gentle force on the handle 12 that transfers a larger force to the guides 16 needed to insert the floss 20 between teeth and then to wipe the tooth surfaces with the floss 20. At the same time the guides 16 move a smaller distance than the rocking travel of the handle 12. As a result, this leverage geometry minimizes initial resistance and dampens the associated overshoot momentum of floss 20 that could otherwise result in poking of the gums. A chamfer 14A (FIG. 8) is formed at the end of each arm 14 in the region of the floss guide 16 to provide clearance for the ends of the arms over the gums of the user.

Reviewing the operation and use of the tool 10, the tool is prepared for use by loading of floss 20. The floss 20 is placed into the floss guides 16 spanning the flossing gap 18. The adjuster is positioned with the passages 28 aligned as seen in FIG. 3 and the floss is laid into the passages 28 and over the forward guide pegs 56. The floss is placed into the floss clamps 40, under the rear guide pegs 56 and into the retainers 54. The clamps 40 are closed with sufficient floss 20 in the floss path 24 to permit formation of a loop at the flossing gap 18. When the clamps 40 are closed, the amount of floss 20 in the floss path 24 is fixed.

The user orients the tool 10 with the gap 18 facing either up or down for flossing of either the upper or lower jaw. By grasping the handle 12 with a single hand, the user can keep the clamps 40 tightly closed between palm and fingers, and also operate the crank 66 or the crank 68 with the thumb.

The bite member 30 is held in the users mouth, for example as seen in FIG. 7, although other locations in the mouth can be used. With the bite member in place, gap 18 is held generally perpendicular to the teeth of the user, and the user manipulates the tool in and out to align the flossing gap 18 with a selected inter tooth crevice. Then with the floss in the gap 18 held in a straight line by rotation of the adjuster 26 to the position of FIG. 7, the user manipulates the tool to force the floss 20 vertically between the adjacent teeth, while keeping light thumb pressure on the crank 66 or 68 to maintain the needed tension.

The floss 20 is then permitted to form a loop by moving the adjuster 26, for example to the position of FIG. 6 or the position of FIG. 3. Then the tool 10 is manipulated with a rocking movement to wipe the tooth surfaces with a vertical motion. The forces in the flossing gap are balanced at all times due to the symmetry of the structure including the two movable floss passages 28 working in unison at opposite sides of the tool. There is no tendency for the floss 20 to move back and forth with an undesirable sawing action. If the floss 20 stretches inelastically, the user can take up the slack by rotation of the length adjuster 26 beyond the position seen in FIG. 7.

At the front of the mouth, it may be more convenient for the user to use the tool 10 without biting the bite member 30 and, instead, to directly move the flossing gap 18 by moving the handle 12. The bite member 30 can move toward the rear of the slots 72 in order not to obstruct this use of the tool 10. When the bite wheel is used at the front of the mouth, the groove 75 accommodates the narrow bite surfaces of the front teeth and the pointed bite surfaces of the corner (canine) teeth, The tool 10 can accommodate many types of floss, including stretchy or stiff, cord or ribbon shape, uniform or non-uniform cross sections and waxed or unwaxed types. At any time in the flossing procedure the user is able to advance a clean segment of floss into the flossing gap 18. When the user relaxes the grip on the handle 12, the clamps 40 are released enough for the user to pull with the other hand on one of the free ends of the floss 20 to move the entire length of floss along the floss path 24.

The tool 10 can be disassembled for cleaning and reassembled easily and without the use of tools. The clamp levers 42 are moved outward beyond their normally open position of FIG. 5 until the tabs 44 move free of the pivot pins 46. The bite member 30 is moved to the rear of the slots 72 until the enlarged ends 74 of trunnions 70 are aligned with an enlarged portion 76 at the rear of each slot 72. The rails 32 can be separated as the enlarged ends 74 move through the enlarged slot portions 76. The studs 36 separate from the sockets 34. The bite member 30 is freed when the rails 32 separate.

Preferably the components of the tool 10 are made of solid or hollow molded plastic materials having the desired characteristic of strength, low cost and light weight. However other materials could be used if desired. The bite member 30 for example could be coated with or made of a somewhat soft and resilient material such as rubber or a similar elastomer.

Referring now to FIGS. 9–12, there is illustrated as another embodiment of the invention a dental flossing tool generally designated as 80. In many respects the tool 80 is similar to the tool 10, and the description of the similarities will not be repeated. Similar elements of tools 10 and 80 are identified with similar reference characters.

Figure 9:
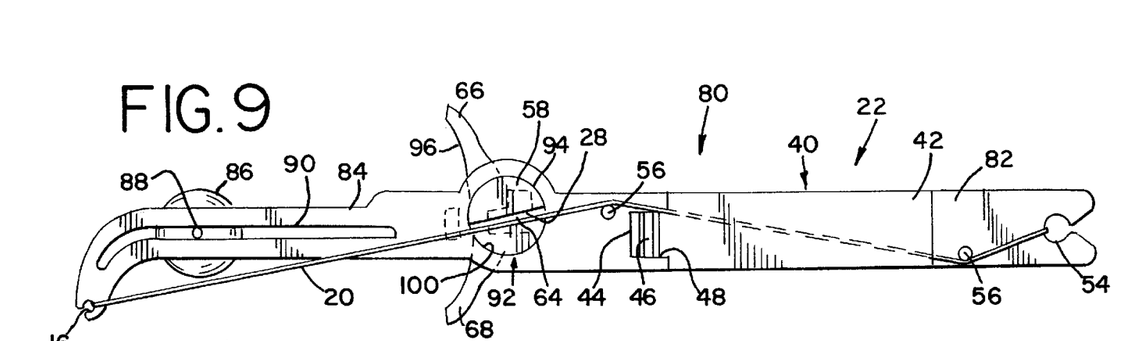
FIG. 9 is a side elevational view of another embodiment of a dental flossing tool constructed in accordance with the present invention.
Figures 10, 11, 12:
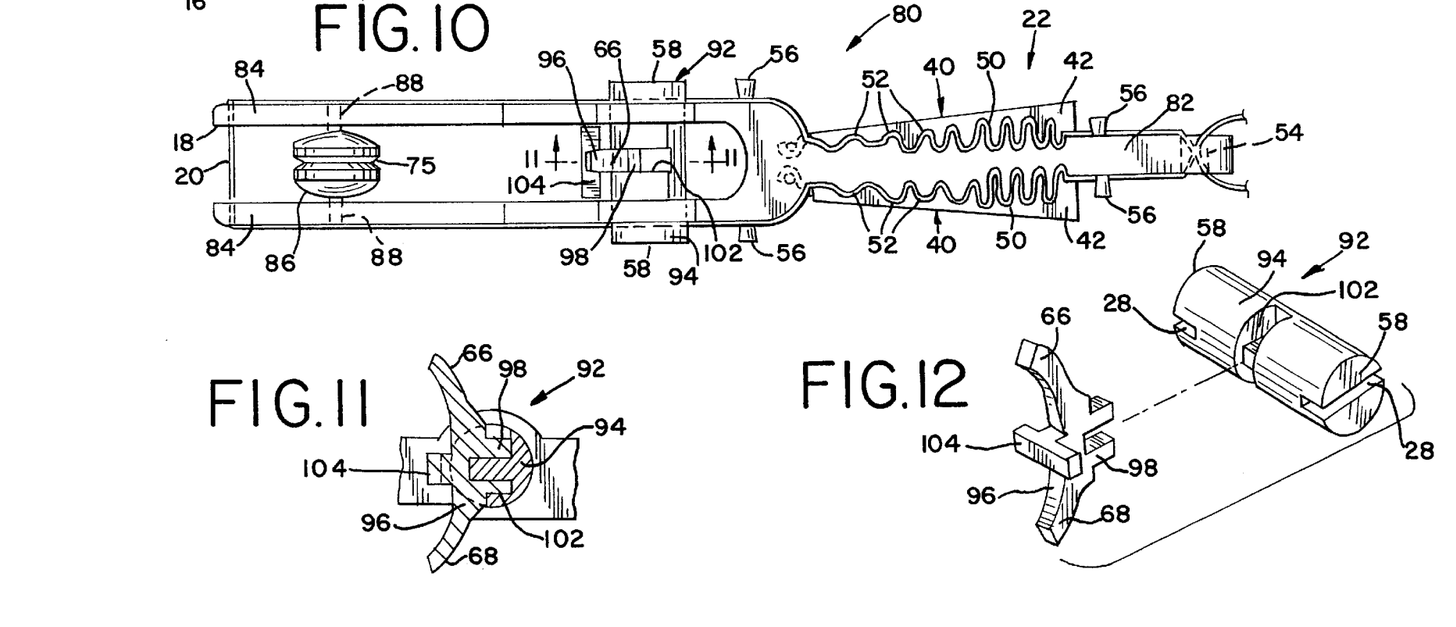
FIG. 10 is a top plan view of the dental flossing tool of FIG. 9.
FIG. 11 is a sectional view taken along the line 11—11 of FIG. 10 illustrating the thumb crank assembly of the dental flossing tool.
FIG. 12 is an exploded isometric view of the thumb crank assembly.

Tool 80 has a one-piece, bifurcated body construction with a generally tubular handle 82 supporting a pair of parallel arms 84. A bite member 86 includes a pair of trunnions 88 received in slots 90. The arms 84 can be resiliently flexed apart for installation of the bite member 86 and the bite member 86 is self centering between the arms 84.

The clamp surfaces 50 are defined on a pair of clamp levers 42 and on opposite surfaces of the one-piece handle 82. Tapered guide pegs 56 are located in front of and behind the clamp levers 42. A single floss retaining recess 54 is provided at the rear portion of the handle 82.

The tool 80 includes a length adjuster 92 having a generally circular cylindrical central barrel member 94 and a crank member 96 including the thumb cranks 66 and 68 and a central portion 98. The barrel member 94 is supported for rotation in aligned openings 100 in the arms 84 and includes a slot 102 at its midsection. The central portion 98 of the crank member 96 is keyed for a press fit into the slot 102. To assemble the length adjuster 92 into the tool 80, the barrel member 94 is inserted from either side through the openings 100 and is centered with respect to the arms 84. The barrel member 94 is rotated so that the slot 102 is facing up or down between the arms 84. Then the crank member 96 is inserted between the arms 84 and the central portion 98 is received with a press fit into the slot 102 to complete the assembly. The crank member 96 includes a spacer bar 104 that centers the length adjuster 92 between the arms 84.

While the present invention has been described with reference to the details of the embodiment of the invention shown in the drawing, these details are not intended to limit the scope of the invention as claimed in the appended claims.

What is claimed is:

1. A dental flossing tool comprising:
   a handle;
   a tip spaced from said handle;
   said tip including a pair of floss guides defining a flossing gap;
   a floss path including said flossing gap;
   an anchor structure for holding a segment of a length of floss in a fixed position in said floss path; and
   a floss path length adjuster spaced from said anchor structure and located along said floss path between said anchor structure and said tip for varying the floss path length in order to alter the configuration and the tension of floss in said gap.

2. The dental flossing tool claimed in claim 1, further comprising a pair of arms having extending portions extending from said handle and having front portions defining said tip, said floss guides being located at said front portions of said arms.

3. The dental flossing tool claimed in claim 2, further comprising an enlarged bite member supported between said extending portions of said arms and projecting vertically beyond said extending portions of said arms.

4. A dental flossing tool as claimed in claim 3, said anchor structure including a pair of clamp levers pivotally mounted for movement toward and away from said handle for engaging spaced ends of a segment of floss in said floss path.

5. The dental flossing tool claimed in claim 1, said length adjuster comprising a member including a floss passage, said member being movable to displace said floss passage relative to said gap.

6. The dental flossing tool claimed in claim 5, further comprising a pair of arms extending from said handle and having front portions defining said tip, said floss guides being located at said front portions of said arms, said length adjuster comprising a rotatable cylinder extending along an axis between said arms, said floss passage extending along a diameter of said cylinder.

7. The dental flossing tool claimed in claim 6, said rotatable cylinder having opposed ends, a groove in each end, said grooves defining a pair of said floss passages, one being adjacent each of said arms.

8. The dental flossing tool claimed in claim 6, further comprising a radially extending operating crank located for engagement by the thumb of a user.

9. A dental flossing tool comprising:

a handle;

a tip spaced from said handle;

said tip including a pair of floss guides defining a flossing gap;

a floss path including said flossing gap;

an anchor structure for holding a length of floss in said floss path;

a floss path length adjuster for varying the floss path length in order to alter the configuration and the tension of floss in said gap;

a pair of arms extending from said handle and having front portions defining said tip, said floss guides being located at said front portions of said arms; and a bite member supported between said arms;

said bite member being mounted in said arms for sliding motion in the direction of the length of said arms to vary the spacing between said bite member and said gap.

10. The dental flossing tool claimed in claim 9, said bite member being rotationally supported between said arms.

11. The dental flossing tool claimed in claim 10, said bite member being a wheel.

12. A dental flossing tool comprising:

a handle;

a tip spaced from said handle;

said tip including a pair of floss guides defining a flossing gap;

a floss path including said flossing gap;

an anchor structure for holding a length of floss in said floss path; and a floss path length adjuster for varying the floss path length in order to alter the configuration and the tension of floss in said gap;

said anchor structure including a lever mounted at a pivot axis for pivotal movement relative to said handle, said handle and said lever having interfacing floss gripping surfaces, said gripping surfaces having rounded undulations;

said undulations having a larger spacing adjacent said pivot axis and a closer spacing farther from said pivot axis.

13. A dental flossing tool comprising:

a handle;

a tip spaced from said handle;

said tip including a pair of floss guides defining a flossing gap;

a floss path including said flossing gap;

an anchor structure for holding a length of floss in said floss path; and a floss path length adjuster for varying the floss path length in order to alter the configuration and the tension of floss in said gap;

said anchor structure including a lever mounted at a pivot axis for pivotal movement relative to said handle, said handle and said lever having interfacing floss gripping surfaces, said gripping surfaces having rounded undulations;

said undulations having a smaller height adjacent said pivot axis and a larger height farther from said pivot axis.

14. A dental flossing tool comprising:

a handle;

a tip spaced from said handle;

said tip including a pair of floss guides defining a flossing gap;

a floss path including said flossing gap;

an anchor structure for holding a length of floss in said floss path;

a floss path length adjuster for varying the floss path length in order to alter the configuration and the tension of floss in said gap;

a pair of arms extending from said handle and having front portions defining said tip, said floss guides being located at said front portions of said arms; and spaced apart rails having front portions defining said arms and having rear portions defining said handle, said anchor structure including a pair of levers each mounted at a pivot axis for movement relative to said rear portion of one of said rails.

15. A dental flossing tool comprising:

a handle;

a pair of arms extending from said handle;

a pair of floss guides at the ends of said arms defining a flossing gap;

a floss anchor structure adjacent said handle for holding ends of a length of floss extending along a floss path including said floss guides and said flossing gap; and an enlarged bite member supported between and projecting vertically beyond said arms.

16. The dental flossing tool claimed in claim 15, said anchor structure including a lever mounted at a pivot axis for pivotal movement relative to said handle, said handle and said lever having interfacing floss gripping surfaces.

17. The dental flossing tool claimed in claim 16 said gripping surfaces having rounded undulations.

18. The dental flossing tool claimed in claim 17, said undulations being sinusoidal.

19. A dental flossing tool comprising:

a handle;

pair of arms extending from said handle;

a pair of floss guides at the ends of said arms defining a flossing gap;

a floss anchor structure adjacent said handle for holding ends of a length of floss extending along a floss path including said floss guides and said flossing gap; and a bite member supported between said arms;

said anchor structure including a lever mounted at a pivot axis for pivotal movement relative to said handle, said handle and said lever having interfacing floss gripping surfaces, said gripping surfaces having rounded undulations;

said undulations having a larger spacing and a lower height adjacent said pivot axis and a closer spacing and a taller height farther from said pivot axis.

20. A dental flossing tool comprising:

a handle;

a pair of arms extending from said handle;

a pair of floss guides at the ends of said arms defining a flossing gap;

a floss anchor structure adjacent said handle for holding ends of a length of floss extending along a floss path including said floss guides and said flossing gap; and a bite member supported between said arms;

said bite member being mounted in said arms for sliding motion in the direction of the length of said arms to vary the spacing between said bite member and said gap.

21. The dental flossing tool claimed in claim 20, said bite member being rotationally supported between said arms.

22. The dental flossing tool claimed in claim 21, said bite member being a wheel.

23. A dental flossing tool comprising:

a handle;

a pair of arms extending from said handle;

a pair of floss guides at the ends of said arms defining a flossing gap; and a floss anchor structure adjacent said handle for holding ends of a length of floss extending along a floss path including said floss guides and said flossing gap said floss anchor structure including a pair of floss clamps for opposite ends of a length of floss held in the tool, said floss clamps each having first and second relatively movable clamp jaws, each jaw having a floss engaging gripping surface.

24. The dental flossing tool claimed in claim 23, one of said clamp jaws of each said floss clamps being defined on said handle, a pair of levers pivotally mounted on said handle, the other of said clamp jaws of each said floss clamps being defined on one of said levers.

25. The dental flossing tool claimed in claim 24, said gripping surfaces having rounded undulations.

26. The dental flossing tool claimed in claim 25, said undulations being sinusoidal.

27. A dental flossing tool comprising:

a handle;

a tip spaced from said handle;

said tip including a pair of floss guides defining a flossing gap;

a floss path including said flossing gap; and an anchor structure for holding a length of floss in said floss path;

said anchor structure including a pair of clamp levers pivotally mounted for movement toward and away from said handle for engaging spaced ends of a segment of floss in said floss path.

* * * * *